(12) United States Patent
Xu

(10) Patent No.: US 12,016,715 B2
(45) Date of Patent: Jun. 25, 2024

(54) CHEST X-RAY SYSTEM AND METHOD

(71) Applicant: KONINKLIJKE PHILIPS N.V., Eindhoven (NL)

(72) Inventor: Yuntao Xu, Suzhou (CN)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 18/279,491

(22) PCT Filed: Dec. 15, 2022

(86) PCT No.: PCT/EP2022/086112
§ 371 (c)(1),
(2) Date: Aug. 30, 2023

(87) PCT Pub. No.: WO2023/117674
PCT Pub. Date: Jun. 29, 2023

(65) Prior Publication Data
US 2024/0041415 A1 Feb. 8, 2024

(30) Foreign Application Priority Data

Dec. 21, 2021 (WO) ................ PCT/CN2021/139929
Dec. 27, 2021 (EP) ..................................... 21217774

(51) Int. Cl.
*A61B 6/46* (2024.01)
*A61B 6/00* (2024.01)

(52) U.S. Cl.
CPC .............. *A61B 6/461* (2013.01); *A61B 6/488* (2013.01); *A61B 6/545* (2013.01)

(58) Field of Classification Search
CPC ......... A61B 6/461; A61B 6/488; A61B 6/545; A61B 6/04; A61B 6/08; A61B 6/50; A61B 6/501; A61B 6/542; A61B 6/4435
See application file for complete search history.

(56) References Cited

U.S. PATENT DOCUMENTS

| | | | |
|---|---|---|---|
| 2005/0265516 A1 | 12/2005 | Haider | |
| 2007/0183567 A1* | 8/2007 | Rotondo | ................ A61B 6/463 378/38 |
| 2009/0285357 A1 | 11/2009 | Khamene | |
| 2014/0348296 A1 | 11/2014 | Goossen | |
| 2015/0003674 A1 | 1/2015 | Eun | |

(Continued)

FOREIGN PATENT DOCUMENTS

| | | |
|---|---|---|
| DE | 102010007654 A1 | 8/2011 |
| JP | 6104618 B2 | 3/2017 |

OTHER PUBLICATIONS

PCT International Search Report, International application No. PCT/EP2022/086112, dated Mar. 15, 2023.

(Continued)

*Primary Examiner* — Courtney D Thomas
(74) *Attorney, Agent, or Firm* — Larry Liberchuk (57) ABSTRACT

A chest X-ray system comprises a camera for capturing video of the patient to be imaged and an X-ray imaging head and X-ray detector. The camera, the X-ray imaging head and the X-ray detector can be translated. The head of the patient is first identified and the chin of the head is identified. The chin is then used as a reference point for translating the camera to a position for chest X-ray imaging.

14 Claims, 8 Drawing Sheets

(56) References Cited

U.S. PATENT DOCUMENTS

| | | |
|---|---|---|
| 2017/0224298 A1 | 8/2017 | Hannemann |
| 2018/0116613 A1 | 5/2018 | Von Berg |
| 2018/0247427 A1 | 8/2018 | Geiger |
| 2021/0121137 A1 | 4/2021 | Vanhooser |
| 2021/0212650 A1* | 7/2021 | Wang .................... G06V 10/98 |

OTHER PUBLICATIONS

Davies, E.K. et al., "Dlib-ml: A Machine Learning Toolkit", Journal of Machine Learning Research, vol. 10, pp. 1755-1758, 2009.

Kazemi V. et al., "One Millisecond Face Alignment with an Ensemble of Regression Trees", Computer Vision and Pattern Recognition, IEEE, 2014:1867-1874.

* cited by examiner

CHEST X-RAY SYSTEM AND METHOD

FIELD OF THE INVENTION

This invention relates to systems and methods for performing a chest X-ray.

BACKGROUND OF THE INVENTION

There are many different diagnostic imaging technologies. Among these, X-ray imaging techniques are widely used for clinical diagnostic medical imaging. There are many different clinical applications, for example for different organs, which can be examined by X-ray medical imaging.

Many hospitals and other medical institutions do not have the facilities to perform even basic imaging procedures because they lack the required position-guiding equipment. If an image is obtained without the correct position control, the image will not be suitable for medical diagnostic imaging, and patients will have to receive a second or even third dose of X-ray radiation due to the inaccurate position control. A high radiation dose is of course undesirable for patient health reasons.

There are various causes of images being obtained which are not suitable for diagnostic purposes, including human error and external factors. Human error for example results from unexperienced doctors, and external factors may include movement by the patient during X-ray imaging. If an image has been taken in unintended position, the patient can be re-positioned and the X-ray images can be re-taken.

It would be preferred to assist the doctor to obtain the correct patient position before X-ray imaging in order to improve the X-ray image quality, increase clinical diagnostic efficiency and optimize clinical workflow.

SUMMARY OF THE INVENTION

The invention is defined by the claims.

According to examples in accordance with an aspect of the invention, there is provided a chest X-ray system, comprising:
 a camera for capturing video of the patient to be imaged;
 an X-ray imaging head and X-ray detector;
 a support system for translating the camera and the X-ray imaging head and X-ray detector;
 a controller; and
 an output system,
 wherein the controller is adapted to:
  translate the camera to a position in which the head of the patient is identified as captured within the video;
  identify the chin of the head;
  use the chin as a reference point for translating the camera, X-ray head and X-ray detector to a position for chest X-ray imaging.

This system is able to translate a camera between a position where it images the head of the patient and a position where it images the chest of the patient. To position the camera in a suitable position for capturing a desired chest X-ray, the camera is first positioned to identify the head of the patient. The camera is moved, or the patient is advised to move, until the head is identified in the camera images.

The chin can then be identified, and this is used as a reference point. The invention is thus based on the recognition that positioning of an X-ray source and X-ray detector for a chest X-ray can be selected using the chin as a reference. This provides a more reliable way to locate a desired camera, X-ray tube source and detector position for the chest X-ray, because the chin to chest distance is more reliable to be fixed within certain distance than the variable chest height between different patients.

The camera is for example mounted on the X-ray tube head with the X-ray source and collimator. The X-ray tube head moves in alignment with the detector. The camera is thus positionally fixed relative to the X-ray head and detector so that the camera location is known in the coordinate space of the X-ray head and detector.

The controller is for example adapted to:
 identify a plurality of features of the head including the chin;
 determine from the identified features the orientation of the head comprising a yaw angle, pitch angle and roll angle relative to a desired orientation of the head;
 determine a required change to the orientation of the head to reach the desired orientation; and
 control the output system to provide instructions to the patient to assist the required change to the orientation of the head before using the chin as a reference point.

Thus, the system ensures the head is in a desired position before using the chin location as a reference point. The desired head orientation for example has the Frankfurt plane perpendicular to the viewing direction of the camera.

The features of the head for example comprise the nose tip, chin, left corner of the left eye and right corner of the right eye, and optionally the left corner of the mouth and right corner of the mouth.

If the yaw angle exceeds a yaw threshold, the instructions for example comprise instructions to turn the head left or right. If the pitch angle exceeds a pitch threshold, the instructions for example comprise instructions to tilt the head up or down. If the roll angle exceeds a roll threshold, the instructions for example comprise instructions to tilt the head left or right.

The controller is preferably further adapted, after translating the camera to a position for chest X-ray imaging, to:
 identify a body position of the patient; and
 control the output system to provide instructions to the patient to assist a required change to a desired body position for a chest X-ray.

In this way, the patient can be instructed to move the body into a desired position which is most suitable for the chest X-ray image.

For example, the controller may be adapted, in order to identify a body position, to identify body features comprising some or all of:
 a spine position between the shoulders;
 a right shoulder;
 a left shoulder;
 a right elbow;
 a left elbow;
 a right wrist;
 a left wrist;
 a mid-spine position; and
 a base spine position.

The controller is then adapted, in order to identify a body position, to determine one or more body shapes comprising:
 an angle of tilt of shoulders about the spine axis;
 lifting of the right or left arm;
 bending of the right or left elbow; and
 bending of the body about the waist,
 and to provide instructions to the patient to remedy undesired body shapes.

The camera is for example a visible light camera. Thus, it is used to detect surface head and body features from the captured images.

The invention also provides a computer-implemented method of preparing a patient for a chest X-ray, comprising:
- translating a camera, X-ray head and X-ray detector to a position in which the head of the patient is identified as captured within a video stream generated by the camera;
- identifying the chin of the head;
- using the chin as a reference point and translating the camera, X-ray head and X-ray detector, or providing instructions to translate the camera, X-ray head and X-ray detector, to a position for chest X-ray imaging using the reference point.

The method may comprise:
- identifying a plurality of features of the head including the chin;
- determining from the identified features the orientation of the head comprising a yaw angle, pitch angle and roll angle relative to a desired orientation of the head;
- determining a required change to the orientation of the head to reach the desired orientation; and
- controlling the output system to provide instructions to the patient to assist the required change to the orientation of the head before using the chin as a reference point.

The method preferably comprises, after translating the camera to a position for chest X-ray imaging:
- identifying a body position of the patient; and
- control the output system to provide instructions to the patient to assist a required change to a desired body position for a chest X-ray.

The invention also provides a computer program comprising computer program code means which is adapted, when said program is run on the controller of the system defined above to implement the method defined above.

These and other aspects of the invention will be apparent from and elucidated with reference to the embodiment(s) described hereinafter.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE EMBODIMENTS

The invention will be described with reference to the Figures.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. It should be understood that the Figures are merely schematic and are not drawn to scale. It should also be understood that the same reference numerals are used throughout the Figures to indicate the same or similar parts.

The invention provides a chest X-ray system, comprising a camera for capturing video of the patient to be imaged and an X-ray imaging head and X-ray detector. The camera, the X-ray imaging head and the X-ray detector can be translated. The head of the patient is first identified and the chin of the head is identified. The chin is then used as a reference point for translating the camera to a position for chest X-ray imaging.

Previously, a doctor had to estimate an accurate patient position for every patient based on the doctor's experience. This is a time-consuming method. The automated approach of the invention does not depend on the experience of different doctors. In particular, a face position is detected and is converted into face landmarks, in particular to identify the chin. This may be achieved by projecting the information from 2D images to 3D points. By analysis of the 3D points information, the head pose can be determined as well as the chin position.

The system can provide guidance to the patient to correct their head pose.

The face recognition is for example combined with body skeleton recognition in order to implement a chest X-ray system. The system thus determines the relative position between the patient head and a patient support (which may be a wallstand panel or a patient couch), and in particular the chin position. Based on this, the system can guide the movement of the patient support (wallstand panel and X-ray head or table) to correctly align the chest area with the X-ray imaging system.

The system can also provide guidance to the patient to correct their body pose, to further remedy an incorrect position during the chest X-ray. The use of the head detection enables the chest height to be determined more accurately, allowing for patients with different heights.

An operation sequence involves the patient stepping (or sitting) on a wallstand or lying on a patient table. The system then gives positioning instructions, so that the doctor can guide the patient to the most suitable position for the chest X-ray. The patient then has the correct position to for the X-ray exposure.

Figure 1:
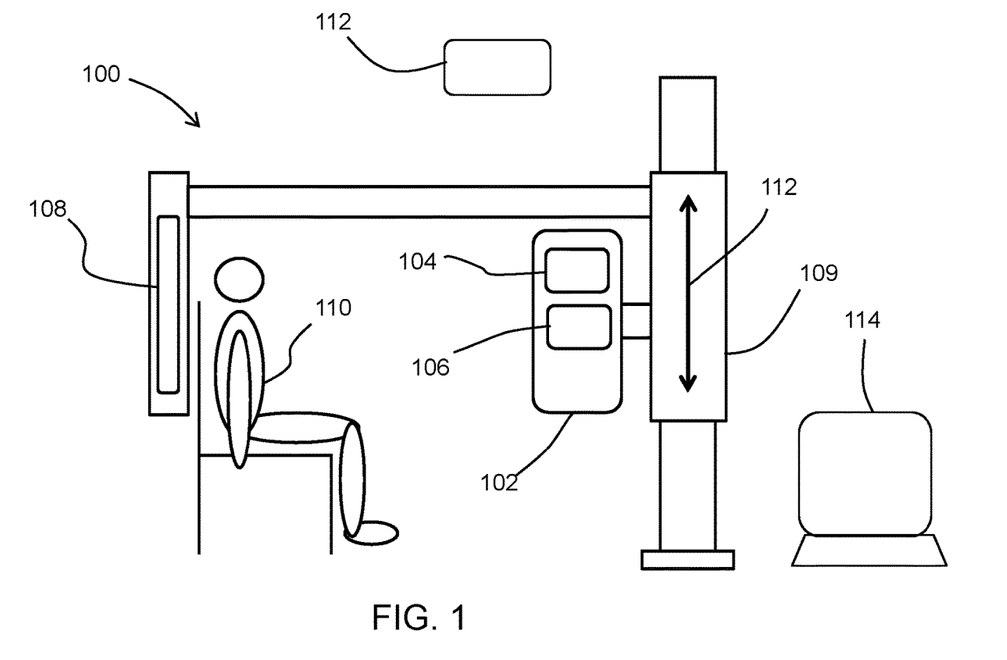
FIG. 1 shows an X-ray system having a wallstand detector for X-ray chest imaging of a patient in a seated position.

FIG. 1 shows an X-ray system 100 having an X-ray head 102 with an X-ray source 104 and camera 106, and an X-ray detector 108. The X-ray detector in this example is part of a wallstand as is used for X-ray chest imaging of a patient 110 in a seated position as shown. The X-ray detector, camera and X-ray source are carried by a support system 109 which can translate them relative to the patient. As discussed below, the camera generates 2D images as well as depth images, e.g. based on time of flight measurements.

The X-ray head 102 (source 104 and camera 106) and X-ray detector 108 have adjustable position (all fixed relative to each other) so that they may be directed to the thorax of the patient or to the head of the patient, by moving the support system 108 as represented by arrow 112.

FIG. 1 shows a controller 112 for processing the camera images and for controlling an output device such as a display 114.

The X-ray detector may instead be part of a patient couch.

Figure 2:
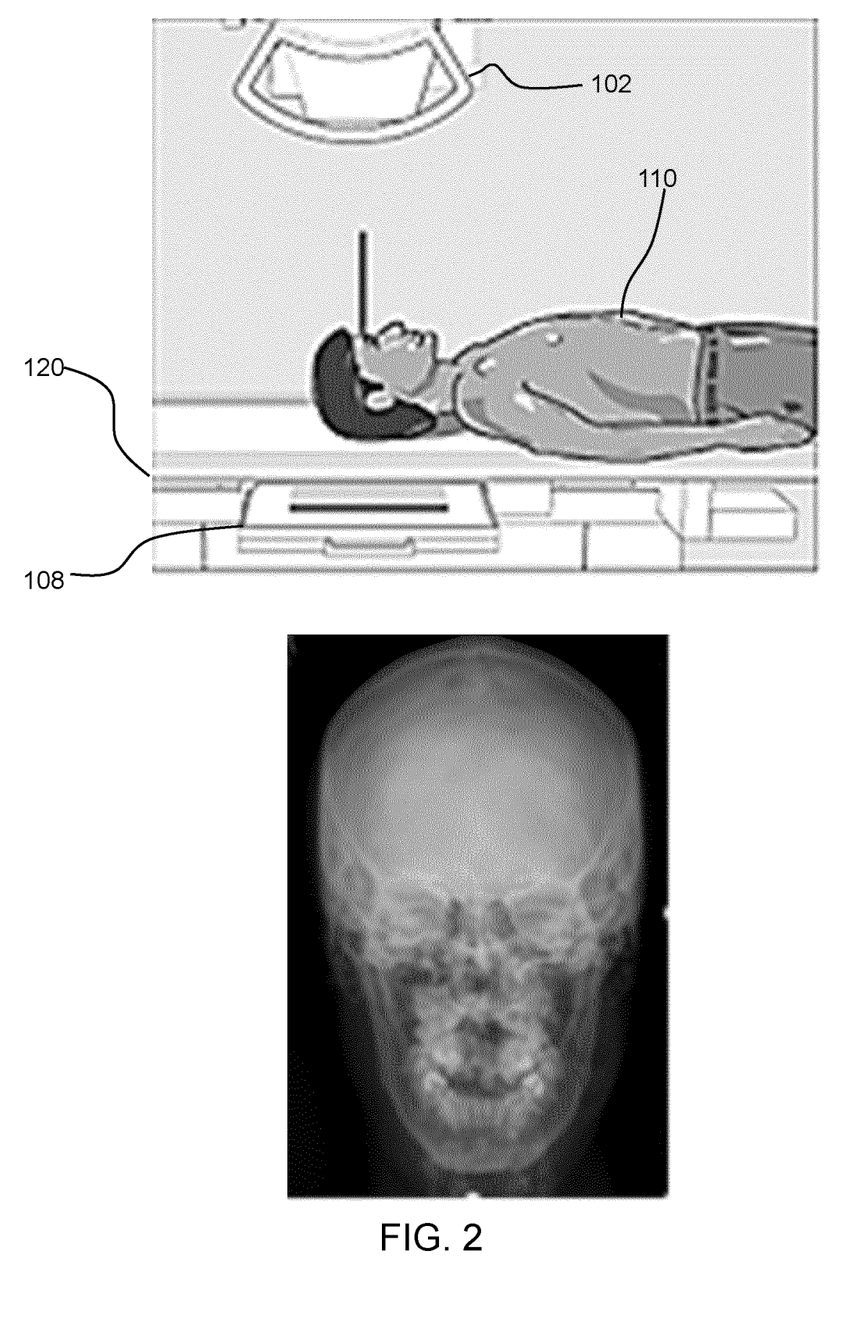
FIG. 2 shows a patient on a couch which incorporates the X-ray detector set up for X-ray imaging of the skull.

FIG. 2 shows the patient 110 on a couch 120 which incorporates the X-ray detector 108, with the X-ray head 102 over the top. FIG. 2 shows the X-ray head 102 aligned with the head of the patient and also shows a resulting X-ray image of the skull.

Figure 3:
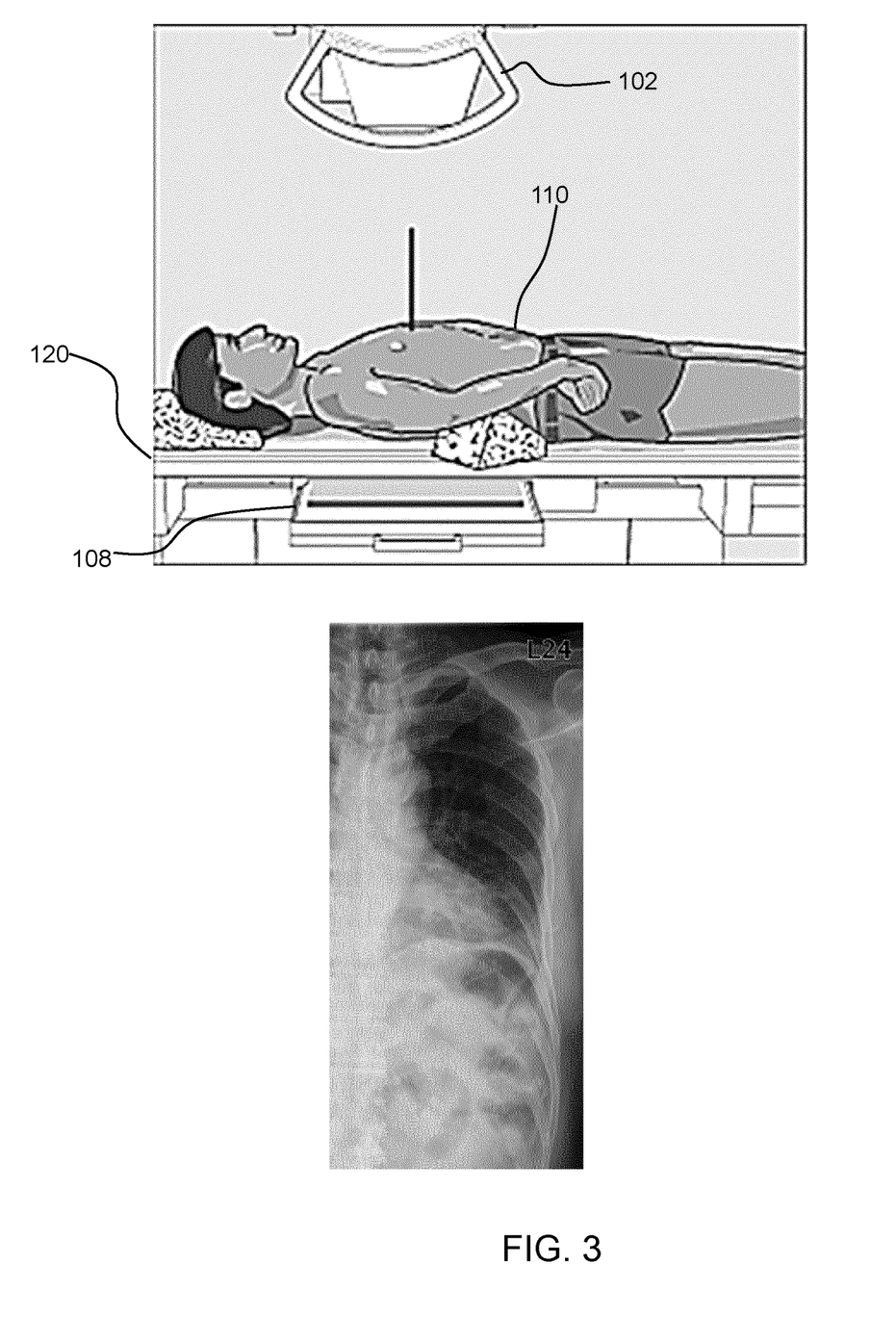
FIG. 3 shows a patient on a couch which incorporates the X-ray detector set up for chest X-ray imaging.

FIG. 3 again shows the patient 110 on a couch 120 which incorporates the X-ray detector 108, and with the X-ray head 102 over the top. FIG. 2 shows the X-ray head 102 aligned with the thorax of the patient and also show a resulting chest X-ray image.

For a head (skull) X-ray, the head is in the anterior-posterior orientation with respect to the X-ray head. The head should be oriented by adjusting the chin position such that the Frankfurt plane is just perpendicular to the X-ray detector.

Figure 4:
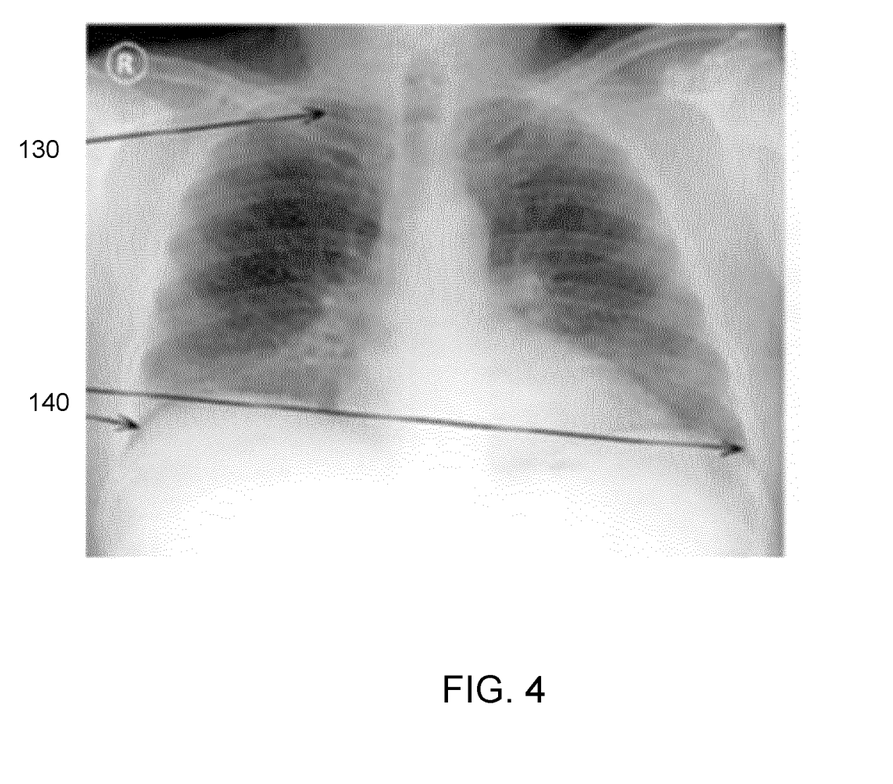
FIG. 4 shows the features that should be visible in a chest X-ray.

For a chest X-ray, there are various features which should be visible as shown in FIG. 4: the top 130 of the lungs, and the lower parts 140 of the diaphragm at both sides, including both costophrenic angles. The lung structure and spine must be discernible behind the heart.

In order to make the top of the lungs visible in images, suitable alignment between the patient and the X-ray head and X-ray detector (e.g. the wallstand detector) is needed. The invention is based on the use of the position of the chin as a reference point. The length between the chin and the top of the lungs is almost constant even for patients of very different height.

Figure 5:
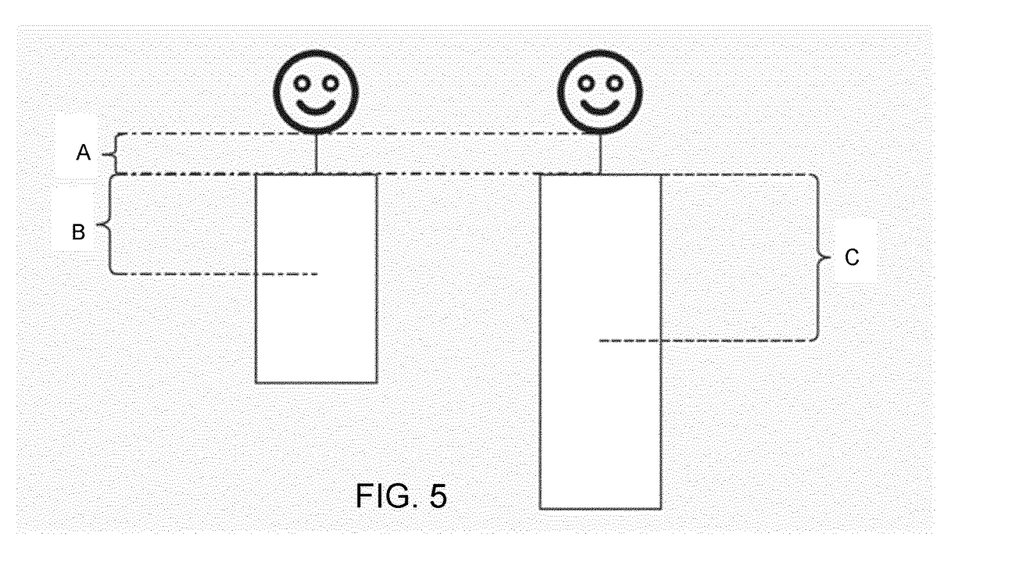
FIG. 5 shows that the length between the chin and the top of the lungs is almost constant even for patients of very different height.

This is schematically illustrated in FIG. 5, where two different height patients are shown. In each case, the distance A between the chin and the top of the lungs is nearly constant, whereas the distance B and C to the mid spine point is different.

When using body points to identify the chest area, these points are for example obtained from the depth information of a 3D camera, and typically a body center point, such as the mid spine point, is used. The distances B and C however differ significantly for different heights of patient. The patient height is typically in a range 1.4 to 1.9 meters.

Figure 6:
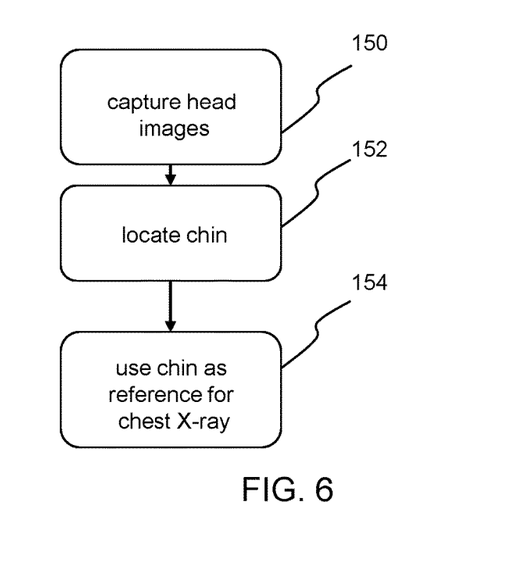
FIG. 6 shows a method of preparing a patient for a chest X-ray.

FIG. 6 shows a method of preparing a patient for a chest X-ray.

In step 150, the camera, X-ray head and X-ray detector are moved to a position in which the head of the patient is identified as captured within a video stream generated by the camera.

In step 152, the chin of the head is identified and in step 154 the chin is used as a reference point and translating the camera, X-ray head and X-ray detector to a position for chest X-ray imaging using the reference point.

Figure 7:
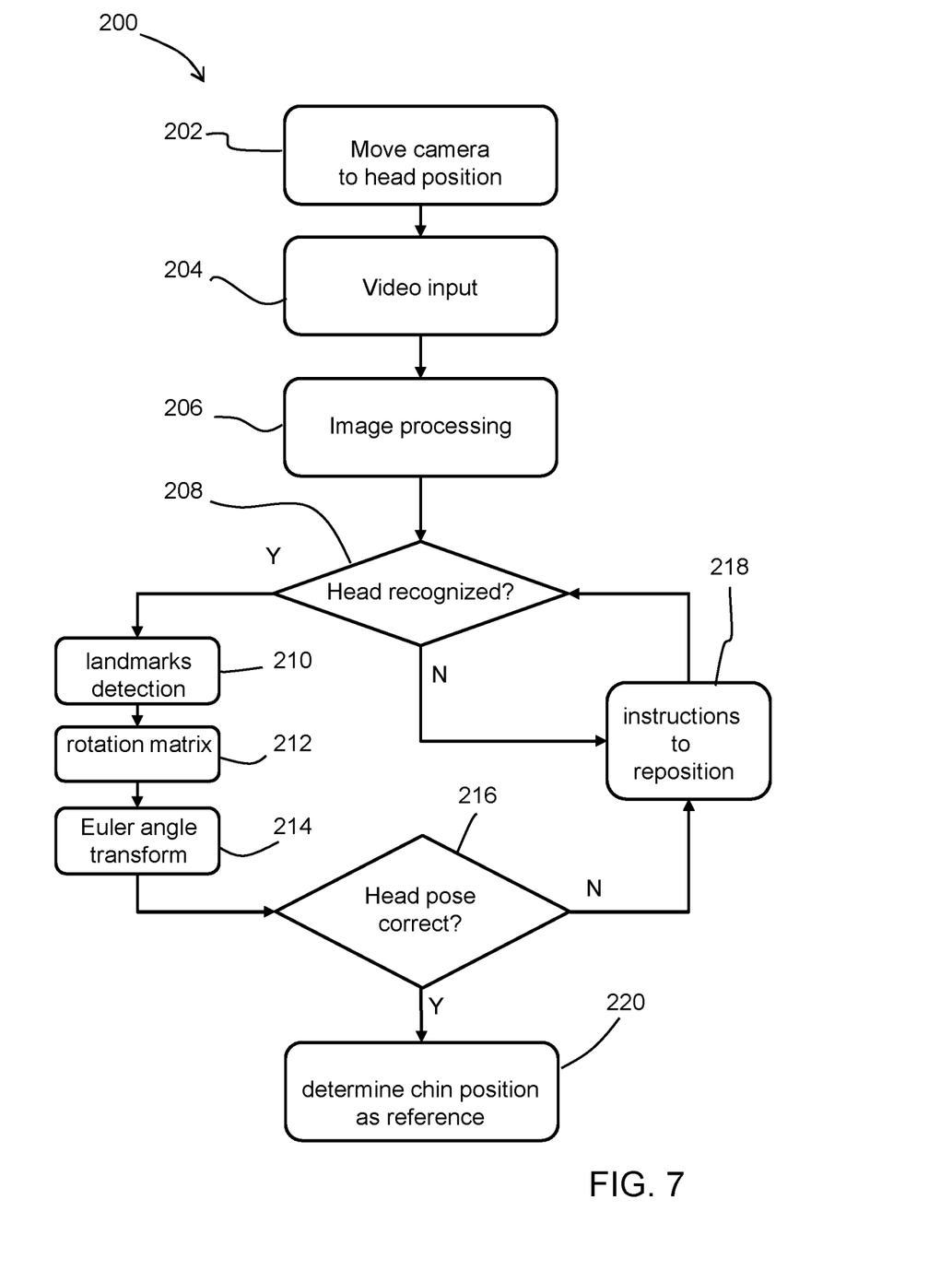
FIG. 7 shows a method for processing images of the head, for obtaining a chin location, and additionally to provide instructions to enable a correct head pose.

FIG. 7 shows a method 200 for processing images of the head, for obtaining a chin location, but additionally to provide instructions to enable a correct head pose.

In step 202, the position of the X-ray head and detector is adjusted to enable X-ray imaging of the head (skull). For example, this involves adjusting the wallstand height to a suitable height position for a skull examination.

The camera takes a video stream of the patient in step 204.

In step 206, there is image processing. This enables in step 208 to determine if a single face can be identified in the camera images.

If a face can be identified, a trained model is used to find face position landmarks in step 210. These landmarks include the chin, as explained above. Based on these landmarks, the algorithm performs recognition using a trained face model.

The algorithm can then determine a face angle, for example using a rotation matrix 212 and a Euler angle transform 214 discussed below.

It is determined if the head pose is correct in step 216. If it is not correct, instructions can be given in step 218 by means of a user interface to assist the doctor and patient in repositioning the head to the desired position.

Once the head is in the correct position the chin is identified as a reference position in step 220.

The camera images used for the head pose are for example the 2D images from the 3D camera. The image pre-processing for example uses a Median blur operation to reduce image noise. The size of the image is derived and the image center point is obtained.

The face landmarks are detected with a known trained model such as Kazemi V, Sullivan J. "One Millisecond Face Alignment with an Ensemble of Regression Trees" Computer Vision and Pattern Recognition. IEEE, 2014:1867-1874.

This model for example obtains six points of the face: nose tip, chin, left eye left corner, right eye right corner, left mouth corner, right mouth corner.

From these six points, a face position judgement is made since the head is to be aligned with the detector, e.g. the wallstand detector. Thus, the face position should be determined relative to the wallstand detector. For this purpose, the center of the images is compared with the position of the face and tolerance values are set. If the center deviation is larger than a certain number of pixels (depending on the detector resolution, e.g. 65 pixels) then an instruction to reposition the head or the X-ray head and X-ray detector (i.e. the wallstand detector) is provided.

Once the deviation is less than the threshold amount, the face is almost in the center of the image plane. The method then performs a judgement of the head pose.

The aim is to judge the locations (U, V, W) of the head as a 3D point P in world coordinates. If a rotation R (a 3×3 matrix) and translation t (a 3×1 vector) are known of the world coordinates with respect to the camera coordinates, the location (X, Y, Z) of each point P in the camera coordinate can be calculated system using the following equation.

$$\begin{bmatrix} X \\ Y \\ Z \end{bmatrix} = R \begin{bmatrix} U \\ V \\ W \end{bmatrix} + t$$

$$\Rightarrow \begin{bmatrix} X \\ Y \\ Z \end{bmatrix} = [R \mid t] \begin{bmatrix} U \\ V \\ W \\ 1 \end{bmatrix}$$

The matrix R and vector t are obtained based on stand coordinates.

If the right pose (R and t) is known, the 2D locations of the 3D facial points on the image can be predicted by projecting the 3D points onto the 2D image. In other words, if R and t are known, a point P in the image can be found for every 3D point being imaged.

Each of the six facial points can thus be mapped to a 3D location in world coordinates. For this purpose, the 3D camera generates color 2D images as well as 3D depth images. These two images are generated by the 3D camera simultaneously.

Thus, 3D point locations for each facial landmark are obtained. The 3D point locations are converted into angles between axes in order to estimate the pose (orientation) of the face.

Firstly, the 3D points are converted into the quaternion number system. The quaternion number system extends the complex numbers. If (x,y,z) is the unit vector of the axis direction, θ is the axis rotation angle. So the quaternion of (x,y,z) can be [cos(θ/2),x*sin(θ/2), y*sin(θ/2), z*sin(θ/2)], which can be represented as (w,x,y,z).

This quaternion can be converted into a Euler Angle by the following formula:

$$\begin{bmatrix} \varphi \\ \theta \\ \psi \end{bmatrix} = \begin{bmatrix} \mathrm{atan2}(2(wx+yz), 1-2(x^2+y^2)) \\ \arcsin(2(wy-zx)) \\ \mathrm{atan2}(2(wz+xy), 1-2(y^2+z^2)) \end{bmatrix}$$

The rotation angles (ψ, θ, φ) represent the yaw, pitch, and roll of the head. After these are obtained, advice can be provided to the patient to adjust their head position according to the set thresholds. For example:

If the yaw is larger than 25 degrees, the patient is advised to turn back to the central position from left or right;

If the pitch is larger than 10 degrees, the patient is advised to turn up or turn down their head to point to the detector; and If the roll is larger than 15 degrees, the patient is advised not to tilt their head to the left or right and keep their head vertical.

Figure 8:
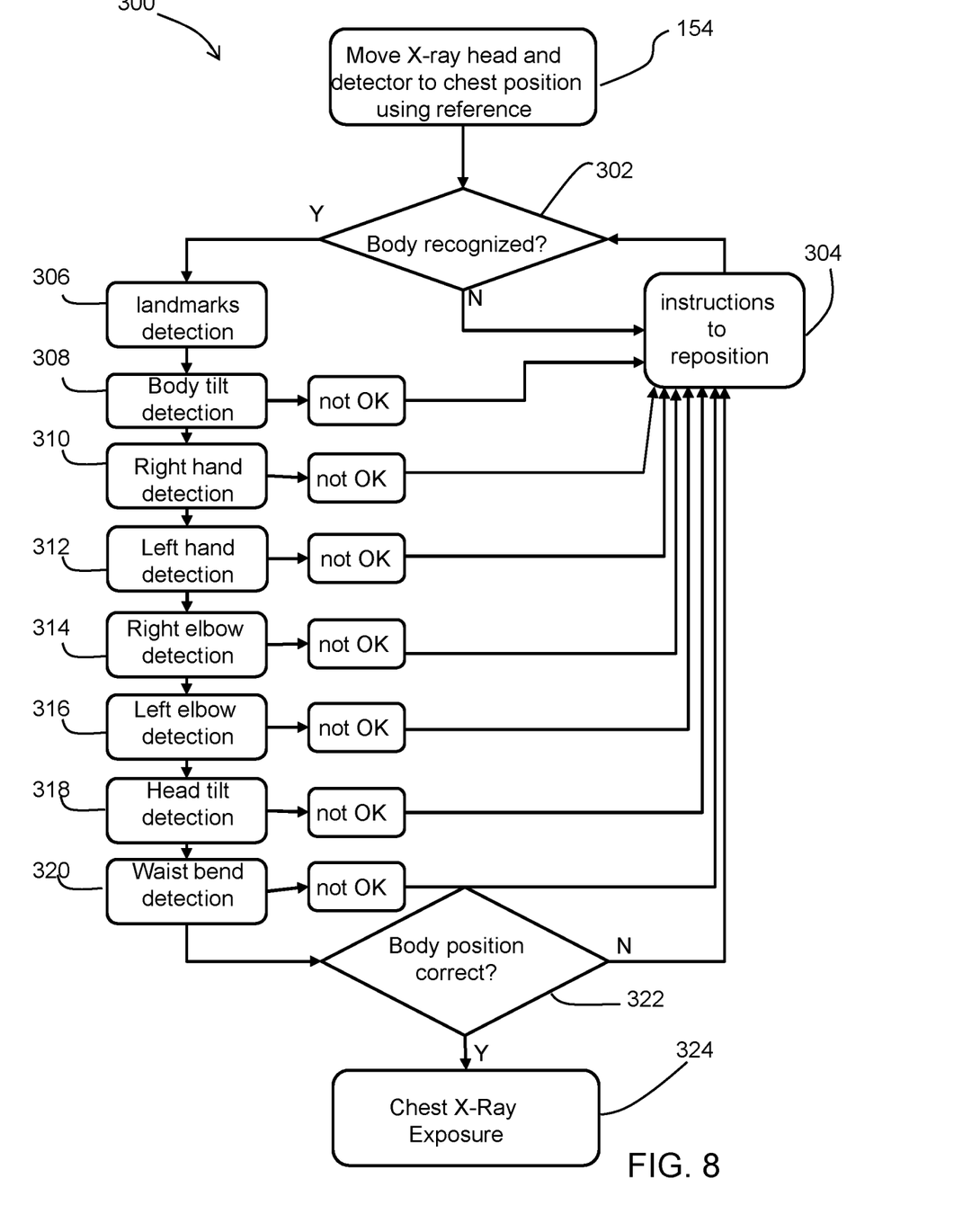
FIG. 8 shows the remainder of the method for preparing for a chest X-ray.

FIG. 8 shows the remainder of the method 300 for preparing for a chest X-ray.

Using the chin location, the camera, X-ray head and X-ray detector are moved to a position for the chest X-ray.

This translation takes place in step 154 (as in FIG. 6). The chin point can for example aligned with the top point of wallstand panel. so this positioning is based on the face position relative to the wallstand detector.

The edge of the image of the wallstand panel is compared with the position of the chin position and a tolerance is set. If the deviation is larger than a threshold then advice is provided: if the chin point is higher, then advice is given to move the wallstand to a higher position. If the chin point is lower, then advice is given to move the wallstand to a lower position.

It may instead be desired to move the top of the wallstand panel to a fixed offset position relative to the chin, e.g. a fixed distance below the chin position, such as 5 cm.

Similarly to the head pose examination, the body position can also be assessed to provide further instructions to the patient (optionally via the doctor) to improve the body position for the chest X-ray.

In step 302 it is determined if the body is recognized. If not, it may be that the patient is too close to the camera, in which case advice and instructions are given in step 304.

For analysis of the body position, the depth images and 2D images from the 3D camera may be used with body skeleton recognition.

Image pre-processing again used Median blur processing to reduce noise.

After it is confirmed that the wallstand height is suitable for the chest X-ray examination, the human body pose is also considered.

For example, if the body is tilted around the vertical axis (e.g. if the patient is in a standing pose rather than a sitting pose), the patient is not standing towards camera (i.e. the X-ray source).

Figure 9:
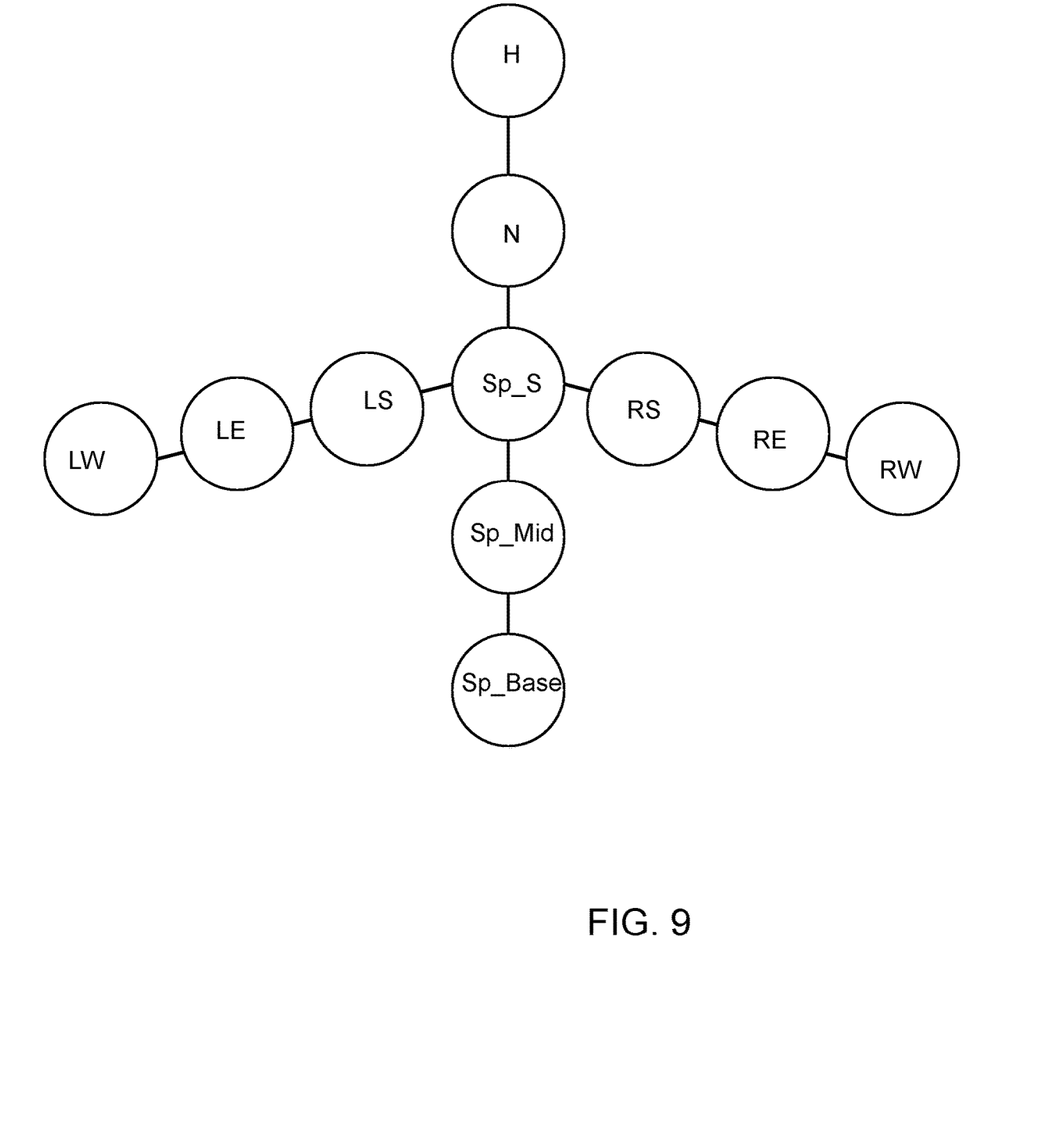
FIG. 9 shows various body landmarks that can be detected

The 3D position of the skeleton can be checked using several points which can be captured through the 3D camera. These points are obtained by landmarks detection in step 306. The points are shown in FIG. 9: Head (H), Neck (N) Spine at the Shoulder height (Sp_S), Left Shoulder (LS), Left Elbow (LE), Left Wrist (LW), Left Hand (LH), Right Shoulder (RS), Right Elbow (RE), Right Wrist (RW), Right Hand (RH), Spine at Mid height (Sp_Mid) and Spine at Base height (Sp_Base).

Based on these points, intersection angles can be calculated between any pair of axes. Each individual axis is defined by two of the points.

Returning to FIG. 8, various angles can be calculated:

In step 308 body tilt is detected. This can be based on the angle between the lines [N to Sp_Mid] and [LS to RS]. If angle is less than 85 degrees advice can be provided to not tilt the body.

In step 310 lifting of the right hand is detected. This can be based on the angle between the lines [Sp_S-RS] and [RS-RE]. If the angle is less than 65 degrees advice can be provided to not lift the right hand.

In step 312 lifting of the left hand is detected. This can be based on the angle between the lines [Sp_S-LS] and [LS-LE]. If the angle is less than 65 degrees advice can be provided to not lift the left hand.

In step 314 bending of the right elbow is detected. This can be based on the angle between the lines [RS-RE] and [RE-RW]. If the angle is larger than 15 degrees advice can be provided to not bend the right elbow.

In step 316 bending of the left elbow is detected. This can be based on the angle between the lines [LS-LE] and [LE-LW]. If the angle is larger than 15 degrees advice can be provided to not bend the left elbow.

In step 318 tilting of the head is detected. This can be based on the angle between the lines [H-N] and [N-Sp_S]. If the angle is larger than 11 degrees advice can be provided to not tilt the head.

The head may remain in the field of view of the camera (with the head in the upper area of the images) even though the X-ray tube head is aligned for a chest X-ray. Thus, the camera typically has a much wider field of view than the X-ray source. For example, the detector size is for example 43 cm×43 cm which corresponds to aa half-angle from the source of 6.8 degrees. One example of 3D camera has a field of view for the depth image of 58.4 degrees (horizontal)× 45.5 degrees (vertical) a field of view for the 2D color image of 63.1 degrees (horizontal)×49.4 degrees (vertical).

In step 320 bending at the waist is detected. This can be based on the angle between the lines [Sp_S-Sp_Mid] and [Sp_Mid-Sp_Base]. If the angle is larger than 11 degrees advice can be provided to not bend at the waist.

Some angle calculations may use four points, for example [N-Sp_Mid] and [RS-LS] for lateral body tilting.

Once the body position is determined as correct in step 322 the Chest X-ray imaging is performed in step 324. If not, advice continues to be provided in step 304 iteratively while the patient adjusts their body position.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality.

A single processor or other unit may fulfill the functions of several items recited in the claims.

The mere fact that certain measures are recited in mutually different dependent claims does not indicate that a combination of these measures cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems.

If the term "adapted to" is used in the claims or description, it is noted the term "adapted to" is intended to be equivalent to the term "configured to".

Any reference signs in the claims should not be construed as limiting the scope.

The invention claimed is:

1. A chest X-ray system, comprising:
a camera for capturing video of the patient to be imaged;
an X-ray imaging head and an X-ray detector;
a support system for translating the camera, the X-ray imaging head, and the X-ray detector; and
a controller configured to:
translate the camera to a position in which a head of the patient is identified as captured within the video;
identify a chin of the head; and
use the chin as a reference point for translating the camera, the X-ray head, and the X-ray detector to a position for chest X-ray imaging.

2. The system of claim 1, wherein the controller is configured to:
identify a plurality of features of the head including the chin;
determine, from the identified features, the orientation of the head comprising a yaw angle, a pitch angle and a roll angle relative to a desired orientation of the head;
determine a required change to the orientation of the head to reach the desired orientation; and
control an output to provide instructions to the patient to assist the required change to the orientation of the head before using the chin as the reference point.

3. The system of claim 2, wherein the desired orientation has the Frankfurt plane perpendicular to the viewing direction of the camera.

4. The system of claim 1, wherein the features of the head comprise the nose tip, chin, left corner of the left eye and right corner of the right eye.

5. The system of claim 1, wherein:
if the yaw angle exceeds a yaw threshold, the instructions comprise instructions to turn the head left or right; and/or
if the pitch angle exceeds a pitch threshold, the instructions comprise instructions to tilt the head up or down; and/or
if the roll angle exceeds a roll threshold, the instructions comprise instructions to tilt the head left or right.

6. The system of claim 1, wherein the controller is further configured, after translating the camera to a position for chest X-ray imaging, to:
identify a body position of the patient; and
control an output to provide instructions to the patient to assist a required change to a desired body position for a chest X-ray.

7. The system of claim 6, wherein the controller is configured, in order to identify a body position, to identify body features comprising some or all of:
a spine position between the shoulders;
a right shoulder;
a left shoulder;
a right elbow;
a left elbow;
a right wrist;
a left wrist;
a mid-spine position; and
a base spine position.

8. The system of claim 7, wherein the controller is configured, in order to identify a body position, to determine one or more body shapes comprising:
an angle of tilt of shoulders about the spine axis;
lifting of the right or left arm;
bending of the right or left elbow; and
bending of the body about the waist,
and to provide instructions to the patient to remedy undesired body shapes.

9. The system of claim 1, wherein the camera is a visible light camera.

10. A computer-implemented method of preparing a patient for a chest X-ray, comprising:
translating a camera, an X-ray head and an X-ray detector to a position in which the head of the patient is identified as captured within a video stream generated by the camera;
identifying a chin of the head;
using the chin as a reference point and translating the camera, the X-ray head and the X-ray detector, or providing instructions to translate the camera, the X-ray head and the X-ray detector, to a position for chest X-ray imaging using the reference point.

11. The method of claim 10, comprising:
identifying a plurality of features of the head including the chin;
determining, from the identified features, the orientation of the head comprising a yaw angle, a pitch angle and a roll angle relative to a desired orientation of the head;
determining a required change to the orientation of the head to reach the desired orientation; and
controlling an output to provide instructions to the patient to assist the required change to the orientation of the head before using the chin as the reference point.

12. The method of claim 11, wherein:
if the yaw angle exceeds a yaw threshold, providing instructions to turn the head left or right; and/or
if the pitch angle exceeds a pitch threshold, providing instructions to tilt the head up or down; and/or
if the roll angle exceeds a roll threshold, providing instructions to tilt the head left or right.

13. The method of claim 10, comprising, after translating the camera to a position for chest X-ray imaging:
identifying a body position of the patient; and
control an output to provide instructions to the patient to assist a required change to a desired body position for a chest X-ray.

14. A non-transitory computer-readable medium for storing executable instructions, which cause a method for preparing a patient for a chest X-ray to be performed, the method comprising:

translating a camera, an X-ray head and an X-ray detector to a position in which the head of the patient is identified as captured within a video stream generated by the camera;
identifying a chin of the head;
using the chin as a reference point and translating the camera, the X-ray head and the X-ray detector, or providing instructions to translate the camera, the X-ray head and the X-ray detector, to a position for chest X-ray imaging using the reference point.

* * * * *